(12) United States Patent
Proksa

(10) Patent No.: US 10,559,393 B2
(45) Date of Patent: Feb. 11, 2020

(54) X-RAY DETECTOR FOR PHASE CONTRAST AND/OR DARK-FIELD IMAGING

(71) Applicant: KONINKLIJKE PHILIPS N.V., Eindhoven (NL)

(72) Inventor: Roland Proksa, Neu Wulmstorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 201 days.

(21) Appl. No.: 15/745,234

(22) PCT Filed: Jul. 20, 2016

(86) PCT No.: PCT/EP2016/067252
§ 371 (c)(1),
(2) Date: Jan. 16, 2018

(87) PCT Pub. No.: WO2017/013153
PCT Pub. Date: Jan. 26, 2017

(65) Prior Publication Data
US 2018/0226168 A1    Aug. 9, 2018

(30) Foreign Application Priority Data
Jul. 21, 2015    (EP) ..................................... 15177714

(51) Int. Cl.
*G01T 1/20* (2006.01)
*G21K 1/06* (2006.01)
(Continued)

(52) U.S. Cl.
CPC ............ *G21K 1/067* (2013.01); *A61B 6/4233* (2013.01); *A61B 6/4291* (2013.01); *A61B 6/484* (2013.01);
(Continued)

(58) Field of Classification Search
CPC ....... A61B 6/42; A61B 6/4208; A61B 6/4266; A61B 6/03; A61B 6/035; G01T 1/003;
(Continued)

(56) References Cited

U.S. PATENT DOCUMENTS 5,144,141 A    9/1992   Rougeot
7,486,770 B2   2/2009   Baumann
(Continued)

FOREIGN PATENT DOCUMENTS

DE    102012217286 A1    3/2014
WO      2010119019 A1   10/2010

OTHER PUBLICATIONS

Rutishauser, Simon et al, "Structured scintillator for hard x-ray grating interferometry" Applied Physics Letters 98, 171107, 2011.

*Primary Examiner* — Don K Wong
(74) *Attorney, Agent, or Firm* — Larry Liberchuk

(57) ABSTRACT

The present invention relates to X-ray imaging. In order to reduce X-ray dose exposure during X-ray image acquisition, an X-ray detector is provided that is suitable for phase contrast and/or dark-field imaging. The X-ray detector comprises a scintillator layer (12) and a photodiode layer (14). The scintillator layer is configured to convert incident X-ray radiation (16) modulated by a phase grating structure (18) into light to be detected by the photodiode layer. The scintillator layer comprises an array of scintillator channels (20) periodically arranged with a pitch (22) forming an analyzer grating structure. The scintillator layer and the photodiode layer form a first detector layer (24) comprising a matrix of pixels (26). Each pixel comprises an array of photodiodes (28), each photodiode forming a sub-pixel (30). Adjacent sub-pixels during operation receive signals having mutually shifted phases. The sub-pixels that during operation receive signals having mutually identical phase form a phase group per pixel. The signals received by the sub-pixels (Continued)

within the same phase group per pixel during operation are combined to provide one phase group signal (32). The phase group signals of different phase groups during operation are obtained in one image acquisition. In an example, the pitch of the scintillator channels is detuned by applying a correcting factor c to a fringe period ($P_{fringe}$) of a periodic interference pattern (35) created by the phase grating structure, wherein $0<c<2$.

13 Claims, 5 Drawing Sheets

(51) Int. Cl.
    *A61B 6/00*    (2006.01)
    *G01N 23/041*    (2018.01)
    *G01T 7/00*    (2006.01)

(52) U.S. Cl.
    CPC ......... *G01N 23/041* (2018.02); *G01T 1/2018* (2013.01); *G01T 7/00* (2013.01); *G21K 2207/005* (2013.01)

(58) Field of Classification Search
    CPC ... G01T 1/1612; G01T 1/1614; G01T 1/1617; G01T 1/1618; G01T 1/1642; G01T 1/20; G01T 1/00
    See application file for complete search history.

(56) References Cited

U.S. PATENT DOCUMENTS

| | | | |
|---|---|---|---|
| 7,522,708 B2 | 4/2009 | Heismann | |
| 7,639,786 B2 | 12/2009 | Baumann | |
| 8,431,902 B2 | 4/2013 | Nakatsugawa | |
| 9,459,355 B1 * | 10/2016 | Zeman | H01L 27/14623 |
| 2003/0047673 A1 | 3/2003 | Thorburn | |
| 2007/0183580 A1 | 8/2007 | Popescu | |
| 2009/0110144 A1 | 4/2009 | Takahashi | |
| 2012/0033785 A1 | 2/2012 | Michel | |
| 2014/0177795 A1 | 6/2014 | Spahn | |
| 2014/0341347 A1 | 11/2014 | Radicke | |
| 2015/0131783 A1 | 5/2015 | Sato | |
| 2015/0182178 A1 | 7/2015 | Baturin | |

* cited by examiner

X-RAY DETECTOR FOR PHASE CONTRAST AND/OR DARK-FIELD IMAGING

CROSS-REFERENCE TO PRIOR APPLICATIONS

This application is the U.S. National Phase application under 35 U.S.C. § 371 of International Application No. PCT/EP2016/067252, filed on Jul. 20, 2016, which claims the benefit of European Patent Application No. 15177714.1, filed on Jul. 21, 2015. These applications are hereby incorporated by reference herein.

FIELD OF THE INVENTION

The present invention relates to the field of X-ray imaging, and more in particular to an X-ray detector, an interferometer, an X-ray imaging system and a method for phase contrast and/or dark-field imaging. Furthermore, the invention relates to a computer program element as well as to a computer-readable medium.

BACKGROUND OF THE INVENTION

X-ray imaging is applied in various technical fields in order to obtain information about internal structures within a region of interest of an object. For example, medical X-ray imaging devices are used to obtain information about internal structures within a patient's body. Phase contrast imaging, e.g. using an interferometer, has been developed to provide higher contrast, especially in soft tissue and other low-absorbing materials. At the same time, the interferometer may also yield a dark-field signal, related to small-angle scattering from structures smaller than the spatial resolution of the detector. The phase information may be acquired using a phase stepping method, which may require multiple exposures. For example, US 2014/0177795 A1 describes an electronic phase stepping method for acquiring the phase information.

SUMMARY OF THE INVENTION

There may be a need to reduce X-ray dose exposures during X-ray image acquisition.

The object of the present invention is solved by the subject-matter of the independent claims, wherein further embodiments are incorporated in the dependent claims. It should be noted that the following described aspects of the invention apply also for the X-ray detector, for the interferometer, for the X-ray system, for the method, for the computer program element, and for the computer readable medium.

According to a first aspect of the present invention, an X-ray detector is provided for phase contrast imaging and/or dark-field imaging. The X-ray detector comprises a scintillator layer and a photodiode layer. The scintillator layer is configured to convert incident X-ray radiation modulated by a phase grating structure into light to be detected by the photodiode layer. The scintillator layer comprises an array of scintillator channels periodically arranged with a pitch forming an analyzer grating structure. The scintillator layer and the photodiode layer form a first detector layer comprising a matrix of pixels and each pixel comprises an array of photodiodes, each photodiode forming a sub-pixel. The adjacent sub-pixels during operation receive signals having mutually shifted phases. The sub-pixels that during operation receive signals having mutually identical phases form a phase group per pixel. The signals received by the sub-pixels within the same phase group per pixel during operation are combined to provide one phase group signal. The phase group signals of different phase groups during operation are obtained in one image acquisition. The pitch of the scintillator channels is detuned by applying a correcting factor c to a fringe period of periodic interference pattern created by the phase grating structure, wherein $0<c<2$.

Advantageously, phase stepping may not be required anymore, because the required phase offsets are measured in one acquisition. Therefore, mechanical or digital shift of the phase grating structure and analyzer grating against each other may not be required. This may also increase the speed of X-ray image acquisition. Furthermore, since phase-contrast signals are extracted in one image acquisition and less X-rays are discarded in the analyzer grating structure compared to the conventional absorber grating, the dose exposures may be reduced without sacrificing the image quality. In addition, the functionality of an analyzer grating structure in form of an array of scintillator channels and the X-ray detector are combined into one unit. The scintillator channels may also have a smaller aperture for incident X-rays compared to the conventional absorber grating, thus increasing the visibility which is a measure for the quality of image acquisition. Furthermore, the design and layout of the X-ray detector may also be simplified by combining signals received by the sub-pixels into a limited number of phase groups, since the number of photodiode channels and readouts are reduced.

The term "pixel", also referred to as "super-pixel", may for example relate to a conventional pixel, which may for example have a diameter of 1 mm. It may be structured into e.g. 1000 sub-pixels of 1 μm.

The term "pitch" in relation with the scintillator channels may also be referred to as channel pitch.

The term "sub-pixel" may also be referred to as photodiode sub-pixel, since it is defined by a photodiode. The sub-pixels may have a sub-pixel pitch, which may be equal or different to the pitch of the scintillator channels.

For example, the sub-pixel pitch is larger than the pitch of the scintillator channels.

In an alternative example, an X-ray detector for phase contrast imaging and/or dark-field imaging is provided that comprises a scintillator layer and a photodiode layer. The scintillator layer is configured to convert incident X-ray radiation modulated by a phase grating structure into light to be detected by the photodiode layer. The scintillator layer comprises an array of scintillator channels periodically arranged with a pitch forming an analyzer grating structure; the scintillator layer and the photodiode layer form a first detector layer comprising a matrix of pixels. Each pixel comprises an array of photodiodes, each photodiode forming a sub-pixel. Adjacent sub-pixels during operation receive signals having mutually shifted phases. The sub-pixels that during operation receive signals having mutually identical phase form a phase group per pixel. The signals received by the sub-pixels within the same phase group per pixel during operation are combined to provide one phase group signal. The phase group signals of different phase groups during operation are obtained in one image acquisition. Further, the detector comprises a second detector layer that is provided on one surface of the first detector layer. One surface is perpendicular to an orientation of the scintillator channels of the first detector layer. The second detector layer comprises a scintillator layer with an array of periodically arranged scintillator channels with the same pitch as the scintillator channels of the first detector layer and a photodiode layer.

Each scintillator channel of the second detector layer is arranged to be displaced in surface direction in relation to the adjacent scintillator channel of the first detector layer by half of the pitch.

In an option, this is also provided in combination with the pitch of the scintillator channels detuned by applying a correcting factor c to a fringe period of periodic interference pattern created by the phase grating structure, wherein 0<c<2.

According to a second aspect of the present invention, an interferometer is provided for phase contrast and/or dark-field X-ray imaging. The interferometer comprises a phase grating structure and an X-ray detector according to one of the examples described above and in the following. The phase grating structure and the X-ray detector are arranged in an optical path such that the phase grating structure and the scintillator layer of the X-ray detector form an interferometer arrangement for correlating X-ray radiation.

The interferometer may also be referred to as grating interferometer. The grating interferometer based X-ray phase contrast imaging may provide superior contrast, especially in soft tissue, when compared to conventional attenuation based imaging. The grating interferometer may also be used to provide a dark-field image that can show details e.g. in biomedical and material science applications.

According to a third aspect of the present invention, an X-ray imagining system is provided. The X-ray imaging system comprises an X-ray source and an interferometer according to one of the examples described above and in the following. The X-ray source is configured to apply X-ray radiation to an object of interest positionable in the optical path to be detected by the X-ray detector of the interferometer.

In an example, the X-ray source is a high brilliant synchrotron source with monochromatic and almost parallel beams.

In a further example, the X-ray source is a conventional, low-brilliance X-ray tube with an additional source grating.

According to a further, fourth aspect of the invention, there is provided a method for phase contrast and/or dark-field X-ray imaging. The method comprises the following steps:

a) generating X-ray radiation modulated by a phase grating structure to examine an object of interest; and
b) converting, by a scintillator layer of an X-ray detector, the modulated X-ray radiation into light and detecting the light by a photodiode layer of the X-ray detector.

In step b), the scintillator layer comprises an array of periodically arranged scintillator channels with a pitch forming an analyzer grating structure. The scintillator layer and the photodiode layer form a first detector layer comprising a matrix of pixels. Each pixel comprises an array of photodiodes, each photodiode forming a sub-pixel. Adjacent sub-pixels during operation receive signals having mutually shifted phases. The sub-pixels that during operation receive signals having mutually identical phase form a phase group per pixel. The signals received by the sub-pixels within the same phase group per pixel are combined to provide one phase group signal. The phase group signals of different phase groups are obtained in one image acquisition. The pitch of the scintillator channels is detuned by applying a correcting factor c to a fringe period of periodic interference pattern created by the phase grating structure, wherein 0<c<2.

According to a fifth aspect of the invention, a computer program element is provided for controlling an apparatus according to one of the embodiments described above and in the following, which, when being executed by a processing unit, is adapted to perform the inventive method.

According to a sixth aspect of the invention, a computer readable medium is provided having stored the program element.

According to an exemplary embodiment of the present invention, the sub-pixels within the same phase group per pixel are electrically connected with each other for combining the signals received by the sub-pixels within the same phase group into one phase group signal. Each pixel further comprises readout electronics configured to receive the phase group signals of different phase groups in one image acquisition.

The combination of signals within the same phase group may greatly reduce the number of photodiode channels and read-outs per pixel. For example, if a pixel comprises 1000 sub-pixels, a combination of signals within the same phase group reduces the number of readout signals from 1000 to 5, when there are five phase groups per pixel. Therefore, less photodiode channels and read-outs are required, which may simplify the design and layout of readout electronics.

In an example of the electrical connection, the sub-pixels within the same phase group per pixel are permanently connected, for example, by a permanent electrical connection scheme.

In this way, the electrical connection is determined in the production process.

In a further example of the electrical connection, the sub-pixels within the same phase group per pixel are switchably connected.

In this way, a user may configure the X-ray detector by changing the electrical connection between sub-pixels.

According to an exemplary embodiment of the present invention, the photodiodes form a continuous or nearly-continuous photosensitive layer of sub-pixels.

In this way, a continuous (without or nearly without intervals) X-ray image is acquired.

The term "continuous" may relate to a continuous extension of the sub-pixels or photodiodes without X-ray insensitive gaps in-between. The term "continuous" may also relate to a continuous extension of the sub-pixels with X-ray insensitive gaps in-between. For example, small X-ray insensitive gaps may exist between photodiodes e.g. due to production constrains.

According to an exemplary embodiment of the present invention, the phase group signals of the different phase groups cover the complete phase of a wavefront of the X-ray radiation modulated by the phase grating structure.

In this manner, the phase group signals represent different relative phases of a complete phase. In other words, this technique synthesizes the phase stepping process, but avoids phase stepping and therefore the delays associated with mechanical movements of a mechanical phase stepping method as well as the delays associated with electronic switching of an electronic phase stepping method.

The term "complete phase" relates to a phase of $2\pi$.

According to an exemplary embodiment of the present invention, the phase group signals per pixel during operation are read out as readout signals.

In other words, all phase group signals per pixel are read out as readout signals. For example, a pixel is structured into e.g. 1000 sub-pixels and every fifth sub-pixel may be electrically connected forming a phase group signal. Only four readout signals are generated per pixel. Therefore, the number of photodiode channels and read-outs can be reduced.

According to an exemplary embodiment of the present invention, when there is an even number of phase group signals per pixel, a sum of all phase group signals per pixel and differences of pairs of phase group signals per pixel with a mutual phase shift of π during operation are read out as readout signals.

As a result, the number of readout signals may be further reduced. When there are N (N is an even number) phase group signals per pixel, the number of readout signals per pixel can be further reduced from N to (N/2+1). For example, if there are four phase group signals per pixel, the number of readout signals per pixel can be reduced to 3. For eight phase group signals per pixel, the number of readout signals per pixel can be reduced to 5.

With the correcting factor, the interferometer is designed such that the pitch of the analyzer grating structure (i.e. the scintillator layer) is detuned in a controlled way. This may be used to generate a fringe pattern causing a (small) phase shift between adjacent scintillator channels. With the photodiode matrix, it is possible to combine signals with the same offset as the scintillator channels, and to read out different phase references, thus avoiding the need of phase stepping.

The periodic interference pattern may be generated by the phase grating structure, e.g. when illuminated with a plane or spherical wave. The fringe period is the periodicity of the fringes on the detection surface of the scintillator layer. The fringe period may be referred to as $p_{fringe}$. Thus, the pitch may be defined as $c*p_{fringe}$. c may be e.g. 0.75, 0.825, 1, 1.125, 1.25, etc.

In case the correcting factor being 1, i.e. the pitch of the scintillator channels is identical to the fringe period, the sub-pixels, i.e. the photodiodes, may have a sub-pixel pitch configured to introduce a mutually shifted phase between adjacent sub-pixels. For example, the sub-pixel pitch may be $1.25*p_{fringe}$, which introduces a phase offset of π/2 between adjacent sub-pixels. Of course, the sub-pixel pitch may have other values, for example, $1.1*p_{fringe}$, $1.125*p_{fringe}$, etc.

In case the correcting factor being different from 1, e.g. c=1.25 (i.e. pitch=$1.25*p_{fringe}$), the adjacent scintillator channels have a phase offset of π/2. Each sub-pixel, i.e. photodiode, may be assigned to a respective scintillator channel. In other words, the sub-pixels have a sub-pixel pitch identical to the pitch—that is, sub-pixel pitch=$1.25*p_{fringe}$. In this manner, adjacent sub-pixels are configured to receive signals with a phase offset of π/2.

According to an exemplary embodiment of the present invention, the X-ray detector further comprises a second detector layer provided on one surface of the first detector layer, which one surface is perpendicular to an orientation of the scintillator channels of the first detector layer. The second detector layer comprises a scintillator layer with an array of periodically arranged scintillator channels with the same pitch as the scintillator channels of the first detector layer and a photodiode layer. Each scintillator channel of the second detector layer is arranged to be displaced in surface direction in relation to the adjacent scintillator channel of the first detector layer by half of the pitch.

In this manner, the scintillator channels of the second detector layer can capture X-rays that pass through the X-ray insensitive gaps between adjacent scintillator channels of the first detector layer, or vice versa. As a result, dose efficiency and visibility may be enhanced.

The X-ray detector with a second detector layer may also be referred to as dual-layer X-ray detector.

According to an exemplary embodiment of the present invention, the X-ray detector further comprises light shield elements provided between two adjacent scintillator channels such that optical crosstalk between said two adjacent scintillator channels is reduced.

The light shield elements between the scintillator channels provide reflection as well as protection against optical crosstalk, which ensures better light output and improved channel-to-channel uniformity.

According to an exemplary embodiment of the present invention, the X-ray imaging system is a medical imaging system, an inspection imaging system, or an industrial imaging system.

There are a number of applications of the X-ray imaging system, both in medical (e.g. some tumours in breast tissue) and other areas, such as the detection of low-absorbing threat objects in security scans, delamination in composite materials, etc. Since phase stepping is unnecessary, the X-ray examination duration may be shortened and the dose utility may be improved.

According to an aspect of the present invention, an X-ray detector is provided for phase contrast and/or dark-field X-ray imaging. The X-ray detector replaces an absorber grating of a conventional interferometer in form of an array of scintillator channels and detection into one unit. The X-ray detector comprises a matrix of photodiodes, each photodiode defining a sub-pixel of a conventional detector pixel. During operation, the sub-pixels that receive signals of same phases are combined to provide one phase group signal. The phase group signals are obtained in one image acquisition. Phase stepping may not be required anymore, because the combined signals of different phase groups represent different relative phases. The absence of an absorber grating may improve the dose utility compared to conventional design and also increase the speed for X-ray image acquisition.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

The present technique is generally directed towards an imaging technique, such as a mammography imaging technique, to generate useful images for medical and non-medical applications. As will be appreciated by those of ordinary skill in the art, the present techniques may be applied in various medical and non-medical applications, such as passenger and/or baggage screening, to provide useful two- or three-dimensional data and context. To facilitate explanation of the present techniques, however, a medical implementation will be generally discussed herein, though it is to be understood that non-medical implementations are also within the scope of the present techniques.

Figure 1:
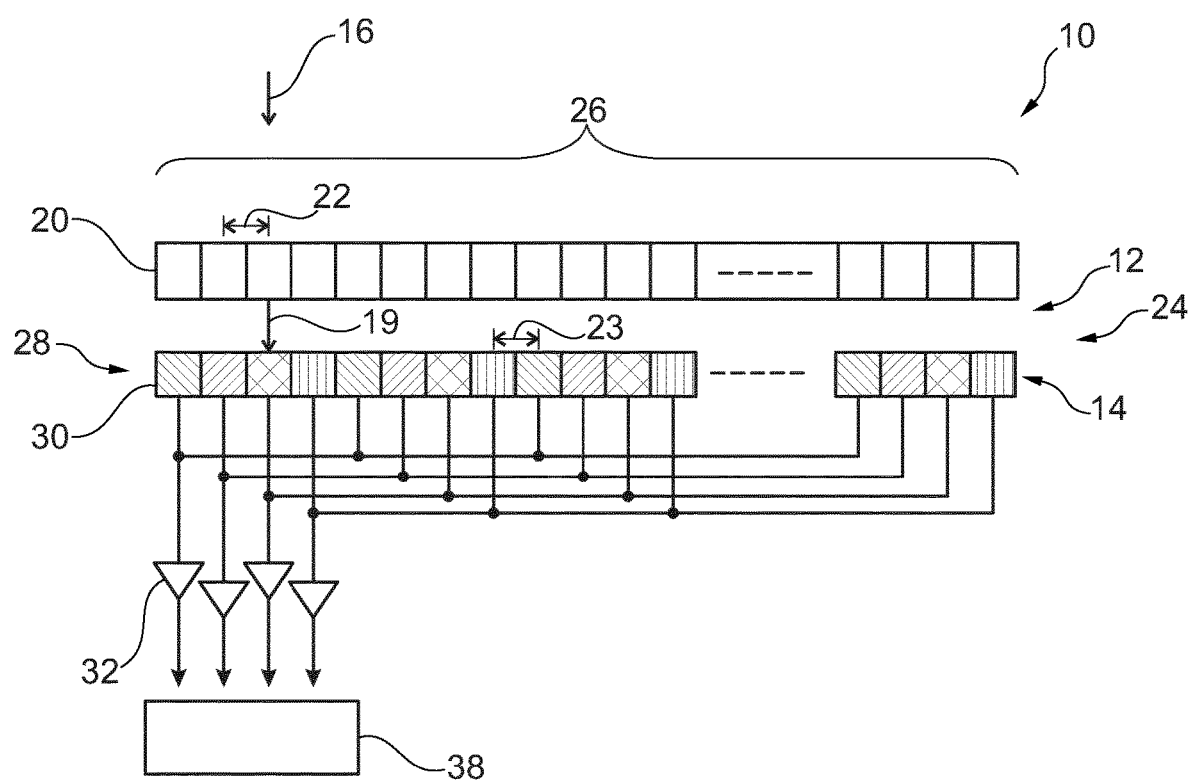
FIG. 1 shows an example of an X-ray detector.

FIG. 1 shows an X-ray detector 10 in accordance with an embodiment of the invention. The X-ray detector 10 comprises a scintillator layer 12 and a photodiode layer 14. The scintillator layer 12 is configured to convert incident X-ray radiation 16 modulated by a phase grating structure 18 (shown in FIG. 2) into light 19 to be detected by the photodiode layer 14. The scintillator layer 12 comprises an array of scintillator channels 20 (illustrated as a grid-like structure) periodically arranged with a pitch 22 forming an analyzer grating structure. The scintillator layer 12 and the photodiode layer 14 form a first detector layer 24 comprising a matrix of pixels 26. Each pixel 26 comprises an array of photodiodes 28, each photodiode forming a sub-pixel 30. For reasons of simplicity, only one pixel 26 is illustrated in FIG. 1 with a plurality of sub-pixels 30, indicated with an array of squares.

Adjacent sub-pixels 30 during operation receive signals having mutually shifted phases. The sub-pixels 30 that during operation receive signals having mutually identical phases form a phase group per pixel. The signals received by the sub-pixels 30 within the same phase group per pixel during operation are combined to provide one phase group signal 32. The phase group signals 32 of different phase groups during operation are obtained in one image acquisition.

The scintillator layer 12 converts X-rays into (visible) light. The scintillator layer 12 may also be referred to as micro-structured scintillator layer, since the scintillator layer 12 comprises an array of scintillator channels 20.

The scintillator channels 20 may for example relate to the micro-columns in a structured scintillator material. The micro-columns are parallel, needle-like structures, which have a diameter from 250 nm (nanometer) to 10 µm (micrometer). They number into the millions per square centimeter yielding very high resolution imaging performance. The structured scintillator material may be prepared for example by vacuum evaporation. Alternatively, micro-columns may be etched into silicon in order to manufacture a matrix that can be filled with a scintillator material like Thallium doped caesium iodide. When X-rays enter those channels, they are converted into light, which is reflected by the micro-columns' sidewalls and thus contained within the micro-columns.

Figure 2:
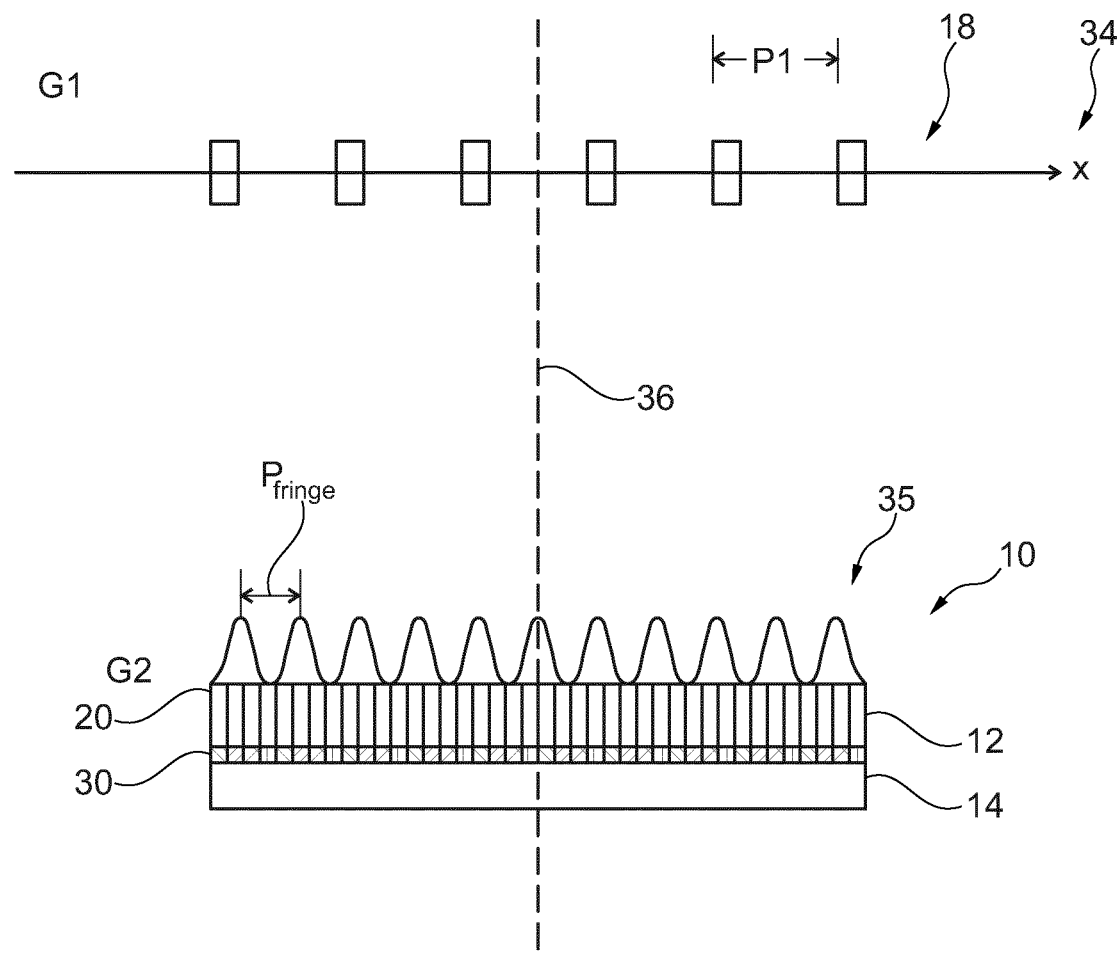
FIG. 2 shows an example of an interferometer.

Now referring to FIG. 2, an interferometer 34 is illustrated for phase contrast and/or dark-field X-ray imaging. The interferometer 34 comprises the phase grating structure 18 and the X-ray detector 10 according to one of the embodiments described above and in the following. The phase grating structure 18 and the X-ray detector 10 are arranged in an optical path 36 indicated with a dashed line, such that the phase grating structure 18 and the scintillator layer 12 of the X-ray detector 10 form an interferometer arrangement for correlating X-ray radiation. The phase grating structure 18 may also be referred to as phase grating structure G1, and the scintillator layer 12 may also be referred to as analyzer grating structure G2. The phase grating structure 18 may have a period of $p_1$ with $\pi$ phase shifting lines, which creates a line interference pattern 35 with a fringe period $p_{fringe}$ on a surface of the scintillator layer 12 with the Talbot self-imaging effect (when there is no object of interest positioned in the optical path 36). The fringe period $p_{fringe}$ of the interference pattern 35 is typically in the order or microns and much smaller than the detector spatial resolution.

The scintillator layer 12 with the array of the scintillator channels 20 functions like an analyzer grating structure, which is used to determine the lateral position and amplitude of the interference pattern, which are related to the differential phase and scattering properties of a sample, for example, an part of an patient. Light converted by the scintillator layer 12 can be detected by the photodiode layer 14.

It is also noted that in FIG. 2, the phase grating structure 18 is illustrated to have a periodicity in one dimension along the x-axis, which thus creates a line interference pattern 35 in the x direction. However, it is appreciated that the phase grating structure 18 may also have a periodicity in the other directions. For example, the phase grating structure 18 may have a periodicity in a direction perpendicular to the x-axis and the optical path 36, which may create a two-dimensional interference pattern. To facilitate explanation of the present techniques, however, a one-dimensional phase grating structure will be generally discussed herein, though it is to be understood that a two-dimensional phase grating structure is also within the scope of the present techniques.

Referring back to FIG. 1, the pixel 26, also referred to as super-pixel, which may for example have a dimension of 1 mm. It may be structured into e.g. 1000 sub-pixels of 1 µm (in FIG. 1, only 16 sub-pixels are depicted).

During operation, adjacent sub-pixels 30 receive signals having mutually shifted phases. The term "mutually shifted phases" relates to the phases that are shifted in relation to each other. It is noted that the mutually shifted phases as used herein refer to the signals being out of phases with each other. Signals with phase difference of $n*2\pi$ (n is an integer) are considered to be in phase, and therefore do not have mutually shifted phases.

In FIG. 1, the sub-pixels 30 that receive signals with different phases (i.e. mutually shifted phases of $\pi/2$) are marked with different grey values or patterns, while the sub-pixels 30 that receive signals with identical phases (i.e. in phase) are marked with same grey value or pattern.

Various methods may be appreciated for achieving a phase shift between adjacent sub-pixels 30.

In an example, the photodiode pitch (i.e. the sub-pixel pitch 23) may be 1/n of the fringe period $p_{fringe}$, where n in an integer larger than 1. The mutual phase shift between adjacent sub-pixels is $2\pi/n$. Every $(n+1)^{th}$ sub-pixel 30 has identical mutually shifted phase and becomes member of the same phase group. FIG. 1 shows an example for n=4.

Figure 3A:
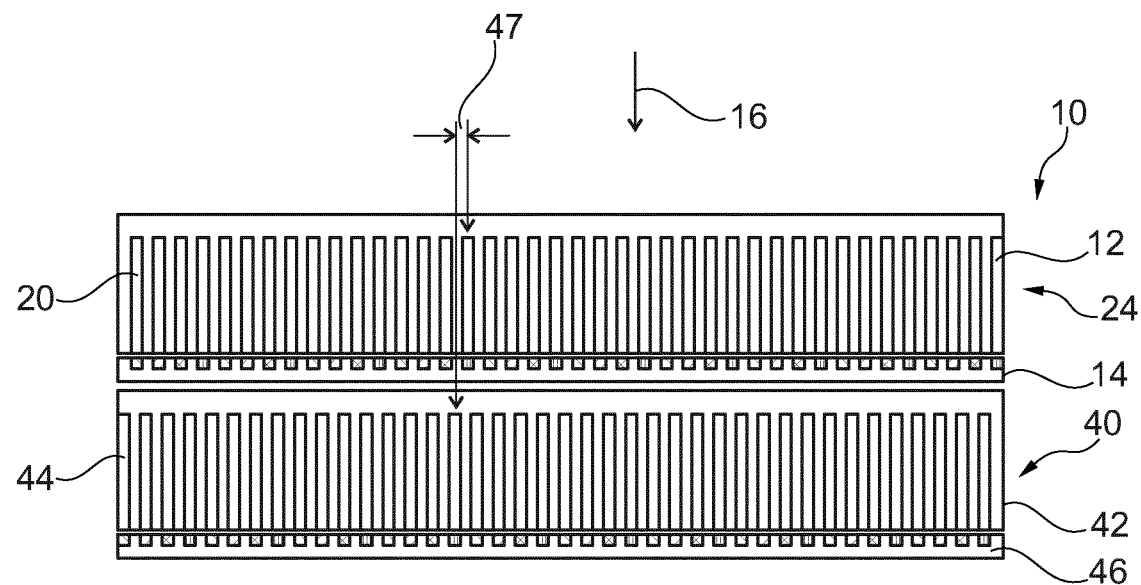
FIGS. 3a and 3b show two further examples of an X-ray detector.
Figure 3B:
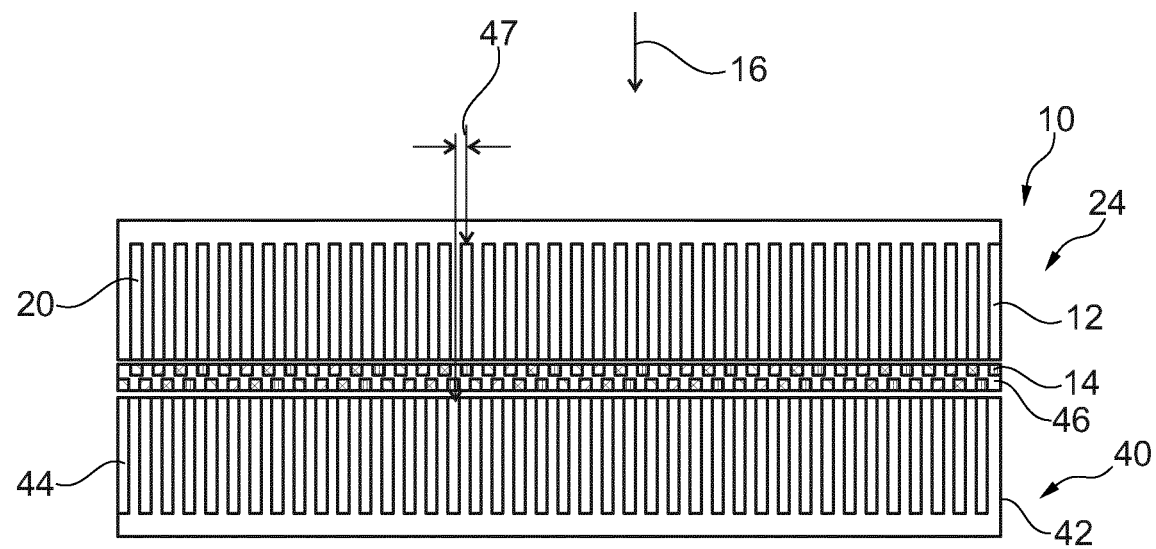

In a further example, the pitch 22 of the scintillator channels 20 may be detuned by applying a correcting factor c to the fringe period $p_{fringe}$ of period interference patterns created by the phase grating structure 18, wherein 0<c<2; that is, pitch=$c*p_{fringe}$. The "detuned" mode may be applicable to a scintillator layer that has X-ray insensitive gaps between adjacent scintillator channels. For example, FIGS. 3a and 3b show scintillator layers with a duty cycle (percentage of one pitch in which X-rays are detected) of 50%. In this manner, adjacent scintillator channels are configured to receive signals having mutually shifted phases. As indicated above, the scintillator channels 20 may be controllable in diameter from 250 nm to 10 µm. Since the pitch 22 of the scintillator channels 20 is arranged to deviate from the fringe period (i.e. pitch≠$p_{fringe}$) a phase shift is introduced between adjacent scintillator channels 20. Each sub-pixel 30, i.e. photodiode 28, may thus be assigned to a respective scintillator channel 20 such that the adjacent sub-pixels 30 during operation receive signals having mutually shifted phases determined by the scintillator channels 20. For example, the correcting factor c is 1.25. In other words, the scintillator layer 12 is designed to have a pitch 22 of 1.25*$p_{fringe}$. Adjacent scintillator channels 20 have a phase offset of $\pi/2$. Every fifth scintillator channels 20 will again have the same phase. Since each scintillator channel 20 is assigned with a photodiode 28, i.e. a sub-pixel 30. Every fifth sub-pixels 30 thus form a phase group of the pixel 26. Likewise, a correcting factor c of 0.75 can also introduce a phase offset of $\pi/2$ between adjacent scintillator channels. Of course, the correcting factor c may also be 0.875, 1.1, 1.125, etc.

It is also noted that the pitch 22 of the scintillator channels 20 as well as the sub-pixel pitch 23 of the sub-pixels 30 as shown in FIG. 1 are for illustrative purposes only. Although the scintillator channels 20 are illustrated to have the pitch 22 identical to the sub-pixel pitch 23 of the sub-pixels 30, it is to be understood that the pitch 22 and the sub-pixel pitch 23 may also be different. For example, the sub-pitch 23 is larger than the pitch 22.

The sub-pixels 30 that during operation receive signals having mutually identical phases form a phase group per pixel.

As indicated above, the term "identical phase", also referred to as in-phase, relates to the situation where the signals have a phase difference of n*$2\pi$, wherein n is an integer.

The phase group is dependent on the sub-pixel pitch of an array of sub-pixels. For example, if adjacent sub-pixels have a phase offset of $\pi/m$, every $(m+1)^{th}$ sub-pixels form a phase group. The minimum number of phase groups in one interferometer period that allows extracting the phase is three in the case of a sinusoidal intensity oscillation. Of course, the adjacent sub-pixels may have smaller phase offset to obtain a better result.

In order to obtain the phase group signals of the same phase group, the sub-pixels within the same phase group per pixel may be electrically connected with each other for combining the signals received by the sub-pixels within the same phase group into one phase group signals 32. Each pixel 26 may further comprise readout electronics 38 configured to receive the phase group signals 32 of different phase groups in one image acquisition.

For example, in FIG. 1, every fifth sub-pixels 30 are configured to receive signals with identical phase. In other words, every fifth sub-pixels 30 form a phase group in the pixel 26. The sub-pixels 30 within the same phase group may be electrically connected (indicated with connected lines) and the received signals may be combined, for example, by sub-unit of the readout electronics 38 that performs addition of signals. The electrical connection may be either permanent (fixed by a permanent electrical connection scheme) or switchable.

The phase group signals 32 of different phase groups are able to be obtained in one image acquisition, or in one imaging step. The phase group signals 32 of the different phase groups may cover the complete phase of a wavefront of the X-ray radiation 16 modulated by the phase grating structure 18.

The phase group signals 32 may be further processed in the readout electronics 38 and read out.

In an example, the phase group signals 32 per pixel during operation are read out as readout signals. In other words, all phase group signals 32 per pixel are read out. For example, in FIG. 1, four phase group signals 32 are read out as four readout signals.

In a further example (not further shown), when there is an even number of phase group signals 32 per pixel, a sum of all phase group signals 32 per pixel and differences of pairs of phase group signals 32 per pixel with a mutual phase shift of it during operation are read out as readout signals.

In other words, if there is an even number of phase group signals 32, there exist pairs of phase group signals 32 with a mutual phase shift of $\pi$. The readout of all phase group signals may be replaced by reading out the sum of all phase group signals 32 and the difference of the signals of all pairs of phase group signals 32 with a mutual phase shift of $\pi$.

For example, when there are N (N is an even number) phase group signals, if the phase group signals are $g_i$ (i=1, 2, . . . , N) and the mutual phase shift of any pair $g_i$ and $g_{i+N/2}$ is $\pi$, the following signals are generated and read out: $g_1+g_2+ \ldots g_N$, $g_1-g_{1+N/2}$, $g_2-g_{2+N/2}$, . . . , $g_{N/2}-g_N$. In this manner, the number of readout signals per pixel is reduced from N to (N/2+1). The required operation to transform the phase group signals to the readout signals may be implemented in the readout electronics, which may be either analogue or digital. In the example of FIG. 1, the number of readout signals per pixel may be further reduced to 3. In a further example, if N is 16, the number of readout signals per pixel may be further reduced to 9.

The number of readout signals may further by reduced if the extraction of the mean intensity, the differential phase and the modulation depth from the acquired phase group signals is generated per super-pixel and read out.

Advantageously, the use of micro-structured scintillator layer as an analyzer grating structure may improve the visibility (a measure for the acquisition quality of the interferometer) of the received signals compared to the conventional absorber grating. In addition, the combination of signals received by the sub-pixels into a limited number of phase groups (e.g. four phase groups in FIG. 1) may reduce the number of photodiode channels and read-outs, thus simplifying the design and layout of the X-ray detector. Since a phase-contrast signal that covers a complete phase of a wavefront of the X-ray radiation is extracted without the need of actual phase stepping (which may imply multiple exposures and low speed), a fast, low-dose, and high sensitive (phase-contrast) X-ray imaging may be achieved.

Further, although only one pixel 26 and 16 sub-pixels 30 are illustrated in FIG. 1, the photodiodes 28 may form a continuous photosensitive layer of sub-pixels 30.

FIG. 3a and FIG. 3b show two further examples of the X-ray detector 10, which comprises X-ray insensitive gaps between adjacent scintillator channels. In FIGS. 3a and 3b, these gaps are illustrated as intervals between adjacent scintillator channels. The X-ray insensitive gaps (or areas) may be formed for example by etching process. X-rays that pass through these gaps cannot be converted into light.

In both examples, a second detector layer 40 is provided on one surface of the first detector layer 24. The surface is perpendicular to an orientation of the scintillator channels 20 of the first detector layer 24. The second detector layer 40 comprises a scintillator layer 42 with an array of periodically arranged scintillator channels 44 with the same pitch as the scintillator channels 20 of the first detector layer 24. The scintillator layer also comprises a photodiode layer 46. Each scintillator channel 44 of the second detector layer 40 is arranged to be displaced in surface direction in relation to the adjacent scintillator channel 20 of the first detector layer 24 by half of the pitch 47.

The term "perpendicular" refers to an angle of approximately 90°, comprising a deviation of +/−15° for example.

In an example, shown in FIG. 3a, the first 24 and the second 40 detector layers are arranged with their photodiode layer 14, 46 and scintillator layers 12, 42 in a stacked order, each detector layer 24, 40 having the same orientation with respect to incoming X-ray radiation 16.

In a further example, shown in FIG. 3b, the first 24 and the second 40 detector layers are arranged in a stacked arrangement with their photodiode layers 14, 46 back to back, the first 24 and second 40 detector layers having an opposite orientation with respect to incoming X-ray radiation 16.

In this manner, X-rays, which pass through the X-ray insensitive gaps between adjacent scintillator channels of the first detector layer, can be detected or captured by the scintillator channels of the second detector layer, or vice versa. X-ray dose utility may thus be improved.

As a further option to the above-mentioned embodiments, light shield elements (not further shown), may be provided between two adjacent scintillator channels 20, 44 such that optical crosstalk between said two adjacent scintillator channels is reduced.

The light shield elements may be either optical filters for selectively transmitting light of different wavelengths, or optical reflectors for selectively reflecting light of different wavelengths. The light shield may be selected to block completely all the light. The light shield elements may be provided as a grid-like or grating-like structure. The light shield elements may be provided with a width of maximum half the pitch width. In case of the light shield elements being transparent to X-ray, by a displacement of the second detector layer of half the pitch, or period, the part of X-ray radiation that has not been affected by the scintillator elements of the first detector layer is also used for image data detection.

Figure 4A:
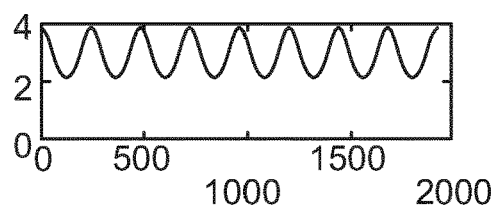
FIG. 4a shows an example of a sampling pattern used in explaining the theory and operation of a conventional phase stepping method.
Figure 4A:
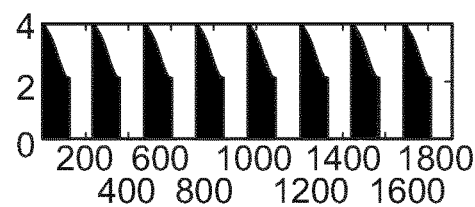
Figure 4A:
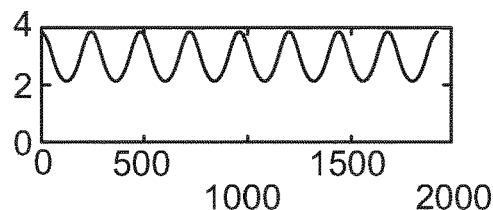
Figure 4A:
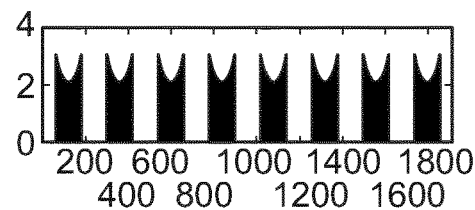
Figure 4A:
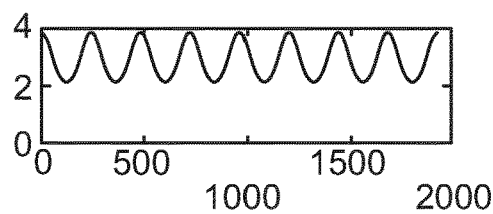
Figure 4A:
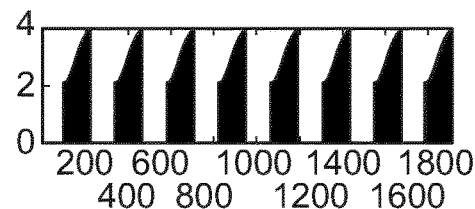
Figure 4A:
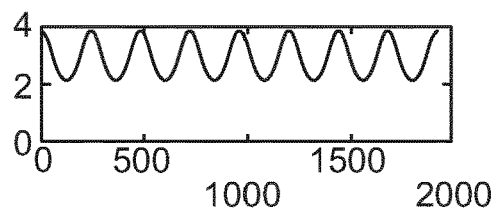
Figure 4A:
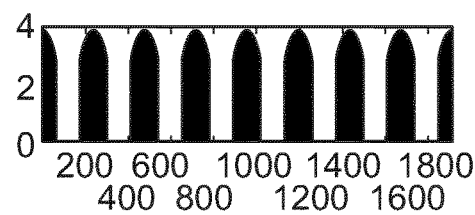
Figure 4B:
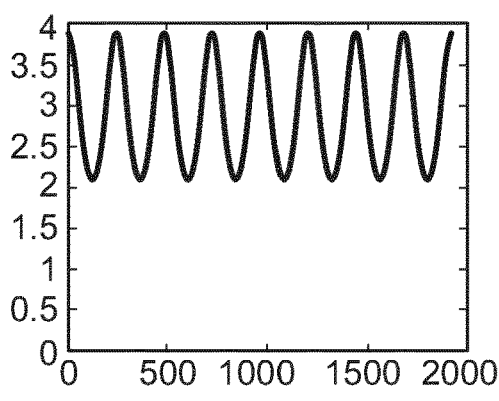
FIG. 4b shows an example of a sampling pattern used in explaining the theory and operation of the X-ray detector according to an example of the invention.
Figure 4B:
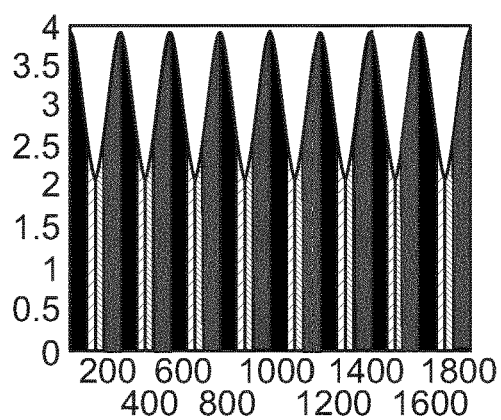

FIG. 4a demonstrates an example of a sampling pattern used in explaining the theory and operation of a conventional phase stepping method, whilst FIG. 4b shows an example of a sampling pattern used in explaining the theory and operation of the X-ray detector 10 according to an embodiment of the invention.

In FIGS. 4a and 4b, the horizontal axis represents the x-axis (arbitrary unit), and the vertical axis represents intensity (arbitrary unit).

A conventional interferometer generates an X-ray wave pattern at the analyzer grating structure $G_2$ with intensity along x of:

$$I(x)=a(1+v\cos(2\pi x/p_{fringe}+\varphi))$$

The following three imaging parameters are needed to be extracted:

a is the mean intensity used to estimate the absorption;

v is the modulation depth of the interferometer coding to estimate dark field signal; and $\varphi$ is the differential phase.

Now looking to just one detector pixel, since the system is not able to provide a higher spatial resolution as the detector resolution, the three parameters are considered to be constant over the pixel under consideration.

The detector resolution is not sufficient to sample the high spatial signal frequency (e.g. $p_{fringe}$~10 μm). The conventional phase stepping method applies the trick to sample the wave with a well-defined spatial frequency of $2\pi/p_{fringe}$ using the analyzer grating structure $G_2$. Behind the analyzer grating structure $G_2$, the "comb-filtered" wave is measured by using a "larger" detector pixel (e.g. 1 mm). The pixel sums the comb-filtered wave over the entire detector pixel. Because the spatial wave frequency matches $p_{fringe}$, the sum of several points of the wave at the same relative phase is obtained. If there is no variation of the three wave parameters, the individual signal contribution should be identical and the detector averaging has no negative impact. The signal wave is obtained by measuring at a well-defined phase. In order to obtain the three imaging parameters, these measurements at different "comb-filter" positions are repeated by shifting the analyzer grating structure $G_2$ (mechanically or digitally). The "large" detector pixel integrates these signals in multiple acquisitions.

The principle of the conventional phase stepping method is demonstrated in FIG. 4a. The left column shows (four times) the wave pattern before the analyzer grating structure $G_2$. The right column shows the comb-filtered signals for four different x offsets (i.e. signals of different phase group). The "large" detector pixel integrates these signals in four acquisitions.

The principle of the X-ray detector 10 according to an embodiment of the invention is illustrated in FIG. 4b. If a high resolution scintillator and a fine structured photodiode array are used, the wave pattern is sampled using the effective comb structure of the photodiode array. For example, if the pitch of the photodiode array is $p_{fringe}/4$, a situation as shown in FIG. 4b is obtained. In FIG. 4b, each photodiode sub-pixel samples one quarter of one fringe period. For data reduction, the signals from all sub-pixel of each pixel with mutually the same phase, i.e. signals from the sub-pixels within the same phase groups in a pixel are combined, e.g. summed. Signals from the same phase groups are indicated with the same gray level in FIG. 4b.

Compared to a conventional phase stepping method as demonstrated in FIG. 4a, phase stepping may not be required anymore because the required phase offsets are measured in one acquisition. Furthermore, the functionality of the analyzer grating structure G2 is replaced with the microstructured scintillator layer 12, which is combined with the X-ray detector into one unit. Since X-rays are neither blocked nor not detected in the structured scintillator design, the dose efficiency may be improved. The visibility may also be improved, because the phase interval integrated by the detector is reduced. In the two examples demonstrated in FIGS. 4a and 4b, a conventional design samples the wave by integration of an interval of $p_{fringe}/2$. This is reduced to an interval of $p_{fringe}/4$ in the example given in FIG. 4b. If we model the effective comb-filtration with a convolution with a rectangle, the frequency response for the interesting spatial frequency is improved from $(\sin(\pi/2))/(\pi/2)\approx 0.64$ to $(\sin(\pi/4))/(\pi/4)\approx 0.9$ giving about 40% better visibility.

Figure 5:
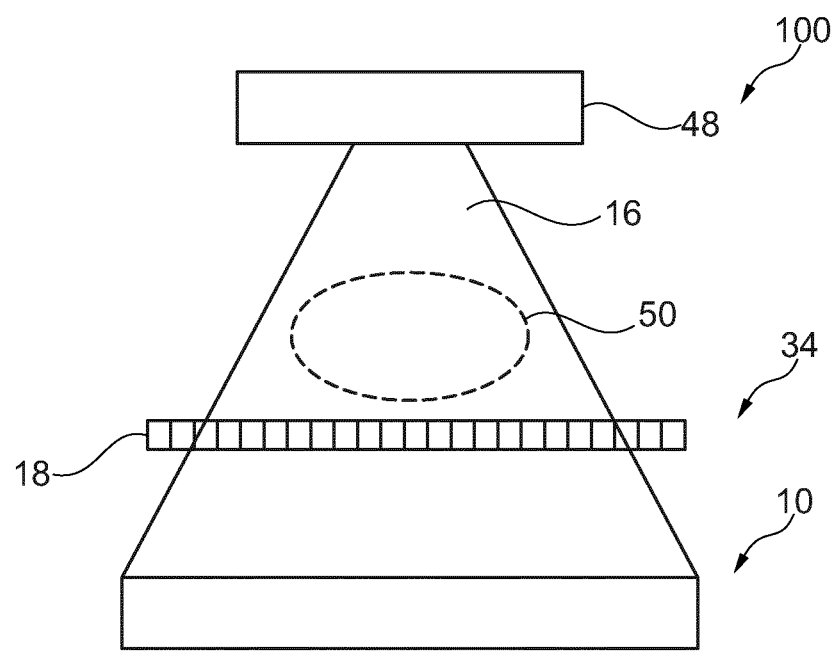
FIG. 5 shows an example of an X-ray imaging system.

FIG. 5 shows an X-ray imaging system 100, comprising an X-ray source 48 and an interferometer according to one of the embodiments described above. The X-ray source 48 is configured to apply X-ray radiation 16 to an object of interest 50 positionable in the optical path 36 to be detected by the X-ray detector 10 of the interferometer 34.

The X-ray source 48 may be a conventional X-ray tube. A source grating structure $G_0$ (not further shown) may be introduced to ensure sufficient spatial coherence. The source grating structure $G_0$ divides the X-ray source 48 into many mutually incoherent line sources, each of which adds constructively (but incoherently) to the interference pattern. Alternatively, the X-ray source 48 may be a source with a spatial coherence, e.g. high brilliant synchrotron radiation sources with monochromatic and almost parallel beam.

Unlike conventional phase stepping method, the phase information can be acquired in one image acquisition. In other words, two major disadvantages (low-speed and multiple exposures) associated with the conventional phase-stepping techniques may be removed (or at least reduced).

The X-ray imaging system 100 may be a medical imaging system, an inspection imaging system, or an industrial imaging system.

The term "medical imaging" relates to irradiating an object with radiation, e.g. X-ray radiation, produced by an X-ray source and to detect the respective attenuation and/or phase information by an X-ray detector. Parts of the energy of the X-ray beam are absorbed when passing the object. On the opposite side of the object of interest, i.e. a portion of patient, a detector or a film captures attenuation and/or phase information, resulting in a medical or clinical image.

The term "inspection imaging system" may also be referred to as security imaging system. For example, airport security luggage scanners use X-rays for inspecting the interior of luggage for security threats before loading on aircraft. Border control truck scanners use X-rays for inspecting the interior of trucks.

An industrial imaging system may be used for inspecting materials for hidden flaws by using the ability of short X-rays to penetrate various materials.

Figure 6:
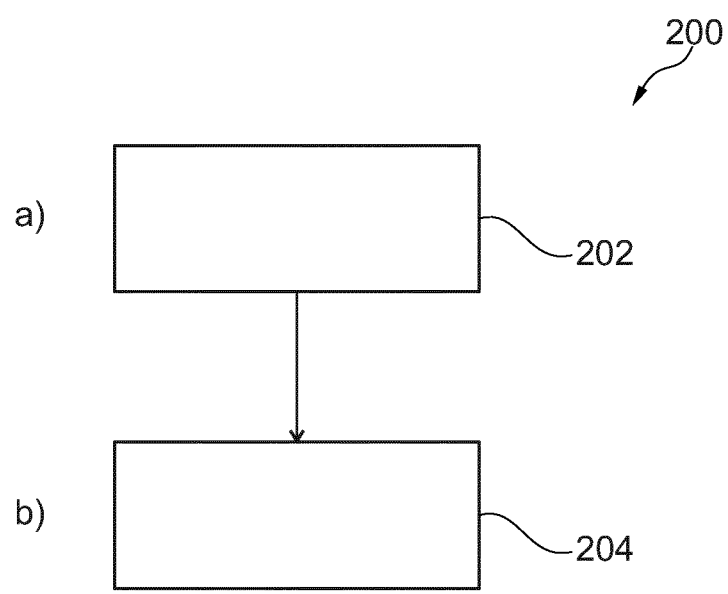
FIG. 6 shows an example of method steps of a method for phase contrast and/or dark-field X-ray imaging.

FIG. 6 shows a method 200 for phase contrast and/or dark-field X-ray imaging. The method comprises the following steps:

In a first step 202, also referred to as step a), X-ray radiation is generated to examine an object of interest, the X-ray radiation being modulated by a phase grating structure.

In a second step 204, also referred to as step b), the modulated X-ray radiation is converted into light by a scintillator layer of an X-ray detector, and the light is detected by a photodiode layer of the X-ray detector.

In the second step 204, i.e. in step b), the scintillator layer comprises an array of periodically arranged scintillator channels with a pitch forming an analyzer grating structure. The scintillator layer and the photodiode layer form a first detector layer comprising a matrix of pixels. Each pixel comprises an array of photodiodes, each photodiode forming a sub-pixel. Adjacent sub-pixels during operation receive signals having mutually shifted phases. The sub-pixels that during operation receive signals having mutually identical phase form a phase group per pixel. The signals received by the sub-pixels within the same phase group per pixel are combined to provide one phase group signal. The phase group signals of different phase groups are obtained in one image acquisition.

In an example, the phase group signals per pixel during operation are read out as readout signals.

In a further example, when there is an even number of phase group signals per pixel, a sum of all phase group signals per pixel and differences of pairs of phase group signals per pixel with a mutual phase shift of it during operation are read out as readout signals.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

The figures are only schematically illustrated and not to scale. Same reference signs refer to same or similar features throughout the figures.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An X-ray detector for phase contrast imaging and/or dark-field imaging, comprising:
a scintillator layer; and
a photodiode layer;
wherein the scintillator layer is configured to convert incident X-ray radiation modulated by a phase grating structure into light to be detected by the photodiode layer;
wherein the scintillator layer comprises an array of scintillator channels periodically arranged with a pitch forming an analyzer grating structure;
wherein the scintillator layer and the photodiode layer form a first detector layer comprising a matrix of pixels
wherein each pixel comprises an array of photodiodes, each photodiode forming a sub-pixel;
wherein adjacent sub-pixels during operation receive signals having mutually shifted phases;
wherein the sub-pixels that during operation receive signals having mutually identical phase form a phase group per pixel;
wherein the signals received by the sub-pixels within the same phase group per pixel during operation are combined to provide one phase group signal;
wherein the phase group signals of different phase groups during operation are obtained in one image acquisition;
wherein the pitch of the scintillator channels is detuned by applying a correcting factor c to a fringe period ($p_{fringe}$) of a periodic interference pattern (35) created by the phase grating structure, wherein $0<c<2$;
wherein the X-ray detector comprises a second detector layer provided on one surface of the first detector layer, which one surface is perpendicular to an orientation of the scintillator channels of the first detector layer;
where the second detector layer comprises a scintillator layer with an array of periodically arranged scintillator channels with the same pitch as the scintillator channels of the first detector layer and a photodiode layer; and
wherein each scintillator channel of the second detector layer is arranged to be displaced in surface direction in relation to the adjacent scintillator channel of the first detector layer by half of the pitch.

2. Detector according to claim 1, wherein the sub-pixels within the same phase group per pixel are electrically connected with each other for combining the signals received by the sub-pixels within the same phase group into one phase group signal; and
wherein each pixel further comprises readout electronics configured to receive the phase group signals of different phase groups in one image acquisition.

3. Detector according to claim 1, wherein the photodiodes form a continuous photosensitive layer of sub-pixels.

4. Detector according to claim 1, wherein the phase group signals of the different phase groups cover the complete phase of a wavefront of the X-ray radiation modulated by the phase grating structure.

5. Detector according to claim 1, wherein the phase group signals per pixel during operation are read out as readout signals.

6. Detector according to claim 4, wherein when there is an even number of phase group signals per pixel, a sum of all phase group signals per pixel and differences of pairs of phase group signals per pixel with a mutual phase shift of 7C during operation are read out as readout signals.

7. Detector according to claim 1, comprising light shield elements provided between two adjacent scintillator channels such that optical crosstalk between said two adjacent scintillator channels is reduced.

8. An interferometer for phase contrast X-ray imaging and/or dark-field X-ray imaging, comprising:
a phase grating structure; and
an X-ray detector according to one of the preceding claims;
wherein the phase grating structure and the X-ray detector are arranged in an optical path such that the phase grating structure and the scintillator layer of the X-ray detector form an interferometer arrangement for correlating X-ray radiation.

9. An X-ray imaging system (100), comprising:
an X-ray source (48); and an interferometer according to claim 8;
wherein the X-ray source is configured to apply X-ray radiation to an object of interest (50) positionable in the optical path to be detected by the X-ray detector of the interferometer.

10. System according to claim 9, wherein the X-ray imaging system is:
a medical imaging system;
an inspection imaging system; or
an industrial imaging system.

11. A method for phase contrast X-ray imaging and/or dark-field X-ray imaging, comprising the following steps:
a) generating X-ray radiation modulated by a phase grating structure to examine an object of interest; and
b) converting, by a scintillator layer of an X-ray detector, the modulated X-ray radiation into light and detecting the light by a photodiode layer of the X-ray detector;
wherein the scintillator layer comprises an array of periodically arranged scintillator channels with a pitch forming an analyzer grating structure;
wherein the scintillator layer and the photodiode layer form a first detector layer comprising a matrix of pixels;
wherein each pixel comprises an array of photodiodes, each photodiode forming a sub-pixel;
wherein adjacent sub-pixels during operation receive signals having mutually shifted phases;
wherein the sub-pixels that during operation receive signals having mutually identical phase form a phase group per pixel;
wherein the signals received by the sub-pixels within the same phase group per pixel are combined to provide one phase group signal;
wherein the phase group signals of different phase groups are obtained in one image acquisition;
wherein the pitch of the scintillator channels is detuned by applying a correcting factor c to a fringe period ($p_{fringe}$) of a periodic interference pattern created by the phase grating structure, wherein $0<c<2$;
wherein the X-ray detector comprises a second detector layer provided on one surface of the first detector layer, which one surface is perpendicular to an orientation of the scintillator channels of the first detector layer;
wherein the second detector layer comprises a scintillator layer with an array of periodically arranged scintillator channels with the same pitch as the scintillator channels of the first detector layer and a photodiode layer; and
wherein each scintillator channel of the second detector layer is arranged to be displaced in surface direction in relation to the adjacent scintillator channel of the first detector layer by half of the pitch.

12. Computer program element for controlling an apparatus, which, when being executed by a processing unit, is adapted to perform the method steps of claim 11.

13. Computer readable medium having stored the program element of claim 12.

* * * * *